United States Patent [19]

McCook et al.

[11] Patent Number: 5,306,486

[45] Date of Patent: Apr. 26, 1994

[54] COSMETIC SUNSCREEN COMPOSITION CONTAINING GREEN TEA AND A SUNSCREEN

[75] Inventors: John P. McCook, Guilford; Alan J. Meyers, Trumbull; Brian J. Dobkowski, Milford, all of Conn.; Allan R. Burger, Passaic, N.J.

[73] Assignee: Elizabeth Arden Co., Division of Conopco, Inc., New York, N.Y.

[21] Appl. No.: 24,711

[22] Filed: Mar. 1, 1993

[51] Int. Cl.$^5$ ............... A61K 7/40; A61K 7/42; A61K 9/10
[52] U.S. Cl. .................. 424/59; 424/60; 424/195.7; 514/938
[58] Field of Search .................. 424/59, 195

[56] References Cited

U.S. PATENT DOCUMENTS

| | | |
|---|---|---|
| 2,418,695 | 4/1947 | Brown .................. 424/59 |
| 2,890,225 | 6/1959 | Gregory ................ 424/59 |
| 5,000,961 | 3/1991 | Lang et al. ........... 424/59 |
| 5,075,102 | 12/1991 | Hubaud et al. ....... 424/59 |

OTHER PUBLICATIONS

Steinmetz, Codex Vegetabilis, Oct. 1959, #505, #677 and #1350.
Carper, The Food Pharmacy, Jul. 1988, pp. 86-90 and 289-296.
Winter, 1952, Handbuch Der Gesamten Parfumerie Und Kosmetik, p. 517.
The Merck Index, 1976, p. 243.
Sagarin, Cosmetics Science & Technology, 1957, p. 199, 200 & 494.
Cancer Letters, 42 (1988) pp. 7-12, by Mukhtar et al.

*Primary Examiner*—Dale R. Ore
*Attorney, Agent, or Firm*—Milton L. Honig

[57] ABSTRACT

A cosmetic composition is provided which includes green tea and a sunscreen compound which is effective to at least partially block ultraviolet radiation from harming human skin, and a pharmaceutically acceptable carrier.

5 Claims, No Drawings

COSMETIC SUNSCREEN COMPOSITION CONTAINING GREEN TEA AND A SUNSCREEN

BACKGROUND OF THE INVENTION

1. Field of the Invention

The invention concerns a cosmetic composition with an improved sunblock system.

2. The Related Art

A tan long has been considered physically attractive and a status symbol. Especially in northern climates, a winter tan advertises the wearer as a person recently returned from a glorious vacation. Tans are also associated with sufficient leisure time and identifying the person as sports oriented.

Unfortunately, recent studies have shown that sunlight can have significant adverse medical effects. Premature skin aging and even cancer have been implicated with exposure to sunlight. These concerns have been heightened by evidence that the earth's ozone layer has suffered severe depletion in recent years. Ozone is recognized as the stratospheric component shielding against the harmful forms of ultraviolet radiation.

Sunscreen formulations for use on human skin are well-known and many different types are commercially available to satisfy diverse consumer needs. For example, sunscreen formulations having different sun protection factor (SPF) values are available, thus allowing consumers to choose the amount of protection desired. SPF values range from zero upward with higher values indicating greater amounts of sun protection. SPF values of 2-4 indicate minimal sun protection, 4-6 indicate moderate sun protection, 8-15 indicate maximal sun protection and above 15 indicate ultra sun protection.

Not only SPF values but aesthetics must be considered in developing consumer acceptable sunscreen compositions. Higher SPF formulas require, of course, higher levels of sunscreen. With inorganic sunscreens higher levels unfortunately leave a visible residue, sometimes referred to as "whitening" on the skin. Whitening detracts from a product's aesthetics. Consumers desire their cosmetics to be unobtrusive, i.e. invisible.

Inorganic sunscreens such as titanium dioxide and zinc oxide are particularly prone to the whitening effect. U.S. Pat. No. 5,028,417 (Bhat et al) sought to overcome the whitening problem through use of an ultrafine titanium dioxide of particle size less than 10 nm. EP 0 433 086 A1 (Cole et al) describes a combination of titanium dioxide and zinc oxide in relative particle sizes of less than 35 nm and 50 nm, respectively.

In the fight against cancer, certain studies have demonstrated that green tea has beneficial effects. Most of the studies relate to antimutagenic effects upon ingestion of this substance. There has, however, been one proposal for topically applying green tea on skin as protection against ultraviolet radiation B-induced photocarcinogenesis in murine skin. See "Proposal to the American Institute for Cancer Research", (Dec. 22, 1989) by Hasan Mukhtar and *Cancer Letters,* 42 (1988) pages 7-12, by Mukhtar et al. While green tea may have some inhibitory effect, there has been little proof that this material can achieve any significant SPF value. Moreoever, green tea, because of its color, also presents aesthetic problems in formulation, especially at the high levels suggested in the art.

Accordingly, it is an object of the present invention to provide a cosmetic composition with a more effective sunscreen system.

Another object of the present invention is to provide a cosmetic composition with a sunscreen system having improved aesthetics when applied onto the skin.

A still further object of the present invention is to provide a cosmetic composition with a sunscreen system that leaves no visible residue or whitening effect when applied onto the skin.

A still further object of the present invention is to provide a cosmetic composition with a sunscreen system having a relatively low human irritancy.

These and other objects of the present invention will more readily become apparent from the description and examples which follow.

SUMMARY OF THE INVENTION

A cosmetic composition is provided including:
(i) from about 0.001 to about 20% by weight of green tea;
(ii) from about 0.001 to about 25% by weight of a sunscreen compound which is effective to at least partially block ultraviolet radiation from harming human skin; and
(iii) from about 30 to 99.9% by weight of a pharmaceutically acceptable carrier.

DETAILED DESCRIPTION OF THE INVENTION

Now it has been discovered that a combination of green tea and a sunscreen compound can provide better ultraviolet radiation protection than either substance separately. Furthermore, the combination provides an invisible topical application when left on the skin.

Green tea as opposed to ordinary tea is unfermented retaining high levels of unoxidized catechins. Fermentation is an enzymatic oxidation process induced by abrasion and aeration of the tea leaves to produce oxidative condensation of catechins that form catechin polymers, such as theaflavins and thearubigins, etc. Major constituents of green tea are (−) epigallocatechin gallate, (−)-epicatechin gallate, (−)epigallocatechin, (+)-gallocatechin, (±)catechin.

For purposes of this invention, green tea is defined as the concentrate extracted from green tea leaves, i.e. tea leaves that have not been aged to destroy the enzyme polyphenoloxidase but have rather been stabilized by moist or dry heat to prevent oxidation of polyphenols. Normally the green tea concentrate is achieved by boiling green tea leaves in water, discarding the leaves while recovering the aqueous solution followed by freeze or spray drying to obtain dried green tea concentrate powder. Alternatively, extraction may be achieved through high pressure extraction with carbon dioxide under supercritical conditions. Green tea concentrate is available from SKW Trostberg Chemicals, Inc., Marietta, Ga. or from the Lipton Tea Company, Englewood, N.J.

Amounts of the green tea will range from about 0.001 to about 20%, preferably from about 0.01 to 10%, optimally between about 0.01 and 1% by weight.

A sunscreen compound is a second necessary component of compositions according to the invention. The term "sunscreen compound" is used to denote ultraviolet ray-blocking compounds inhibiting absorption within the wavelength region between 290 and 420 nm. These compounds may either be organic or inorganic.

Most preferred are the inorganic sunscreens which include titanium dioxide, zinc oxide, iron oxide and combinations thereof. Most preferred is titanium dioxide, especially having an average particle size no higher than 700 nm, preferably no higher than 200 nm, optimally less than 35 nm.

Organic sunscreens suitable for the present invention may be classified into five groups based upon their chemical structures: para-amino benzoates; salicylates; cinnamates; benzophenones; coumarins, azoles and miscellaneous chemicals including menthyl anthralinate. Also polymeric particles may be useful such as polyethylene and polyamides. Among FDA-approved sunscreens are those listed in the Table below.

| | Approved % |
|---|---|
| UV-A Absorbers | |
| Oxybenzone, also known as 2-hydroxy-4-methoxy benzophenone, and benzophenone-3, available as Uvinul M-40 and Gafsorb 2H4M | 2-6 |
| Dioxybenzone, also known as 2,2 dihydroxy-4-methoxy benzophenone, and benzophenone-8 | 3 |
| Sulibenzone, also known as 2-hydroxy-4-methoxy benzophenone-5-sulphonic acid, and benzophenone-4, available as Uvinul MS-40 and Gafsorb 2H4MS | 5-10 |
| Menthyl anthralinate, also known as menthyl-o-aminobenzoate | 3.5-5 |
| UV-B Absorbers | |
| p-Amino benzoic acid, also known as PABA | 5-15 |
| Amyl dimethyl PABA (NA), also known as amyl-p-dimethyl ammonium benzoate, available as Padimate A | 1-5 |
| 2-Ethoxy ethyl p-methoxy cinnamate (NA), available as Cinoxate and Givtan-F | 1-3 |
| Diethanolamine p-ethoxy cinnamate, also known as DEA methoxy cinnamate, available as Parsol-Hydro | 8-10 |
| Digalloyl trioleate (NA), a component of Solprotex I | 2-5 |
| Ethyl-4-bis (hydroxypropyl) aminobenzoate, also known as ethyl dihydroxy propyl PABA, available as Amerscreen P | 1-5 |
| 2-Ethyl hexyl-2-cyano-3,3 diphenyl acrylate, also known as octocrylene and available as Uvinul N-539 | 7-10 |
| Ethyl hexyl p-methoxy cinnamate, also known as octyl methoxycinnamate available as Parsol MCX | 2-7.5 |
| 2-Ethyl hexyl salicylate, also known as octyl salicylate | 3-5 |
| Glyceryl aminobenzoate, also known as glyceryl p-aminobenzoate and glyceryl PABA, available as Escalol 106 | 2-3 |
| Homomenthyl salicylate, also known as 3,3,5-trimethylcyclohexyl salicylate | 4-15 |
| Lawsone with dihydroxyacetone (NA) | 0.25 with 3 |
| Octyl dimethyl PABA, also known as 2-ethyl hexyl p-dimethyl p-aminobenzoate, and 2-ethyl hexyl dimethyl PABA, available as Padimate O and Escalol 507 | 1.4-8 |
| 2-Phenyl benzimidazole 5-sulphoic acid | 1.4 |
| Triethanolamine salicylate | 5-12 |

Amounts of the sunscreen compound will range anywhere from about 0.001 to 25%, optimally to about 15%, most preferably between about 10 and 13% by weight.

Compositions of the present invention may either be solid or liquid, aqueous or anhydrous and opaque or transparent. Most preferably, cosmetic compositions of this invention will be in emulsion form. By definition, an emulsion is a dispersed system containing at least two immiscible liquid phases, one of which is dispersed in the form of small droplets throughout the other. Water and oil are the most common immiscible phases. An emulsion in which oil is dispersed as droplets throughout the aqueous phase is termed an oil-in-water emulsion. When water is the dispersed phase and an oil is the dispersion medium, a water-in-oil emulsion exists. Contemplated within the scope of this invention are emulsions in the form of lotions and creams of both types of emulsions, those where the water phase is continuous and those where the oil phase is continuous. The amount of these phases may range from about 99:1 to 1:99 by weight.

The term "pharmaceutically acceptable carrier" according to this invention includes emollients, surfactants, humectants and water. Total amount of the carrier may range from about 30 to about 99.9%, preferably from about 50 to about 90%, optimally from about 70 to about 85% by weight.

A variety of oily emollients may be employed in the compositions of this invention. These emollients may be selected from one or more of the following classes:

1. Hydrocarbon oils and waxes. Examples thereof are mineral oil, petrolatum, paraffin, ceresin, ozokerite, microcrystalline wax, polyethylene, and perhydrosqualene.
2. Triglyceride esters such as vegetable and animal fats and oils. Examples include castor oil, cocoa butter, safflower oil, cottonseed oil, corn oil, olive oil, cod liver oil, almond oil, avocado oil, palm oil, sesame oil, squalane, and soybean oil.
3. Acetoglyceride esters, such as acetylated monoglycerides.
4. Ethoxylated glycerides, such as ethoxylated glyceryl monostearate.
5. Alkyl esters of fatty acids having 10 to 20 carbon atoms. Methyl, isopropyl, and butyl esters of fatty acids are useful herein. Examples include hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate.
6. Alkenyl esters of fatty acids having 10 to 20 carbon atoms. Examples thereof include oleyl myristate, oleyl stearate, and oleyl oleate.
7. Fatty acids having 10 to 20 carbon atoms. Suitable examples include pelargonic, lauric, myristic, palmitic, stearic, isostearic, hydroxystearic, oleic, linoleic, ricinoleic, arachidic, behenic, and erucic acids.
8. Fatty alcohols having 10 to 20 carbon atoms. Lauryl, myristyl, cetyl, hexadecyl, stearyl, isostearyl, hydroxystearyl, oleyl, ricinoleyl, behenyl, erucyl, and 2-octyl dodecanyl alcohols are examples of satisfactory fatty alcohols.
9. Fatty alcohol ethers. Ethoxylated fatty alcohols of 10 to 20 carbon atoms including the lauryl, cetyl, stearyl, isostearyl, oleyl, and cholesterol alcohols, having attached thereto from 1 to 50 ethylene oxide groups or 1 to 50 propylene oxide groups.
10. Ether-esters such as fatty acid esters of ethoxylated fatty alcohols.
11. Lanolin and derivatives. Lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin alcohols, lanolin alcohols linoleate. lanolin alcohols ricinoleate, acetate of lanolin alcohols ricinoleate, acetate of ethoxylated alcohols-esters, hydrogenolysis of lanolin, ethoxylated hydrogenated lanolin, ethoxylated sorbitol lanolin, and liquid and semisolid lanolin absorption bases are illustrative of emollients derived from lanolin.

12. Polyhydric alcohol esters. Ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol polyfatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

13. Wax esters such as beeswax, spermaceti, myristyl myristate, stearyl stearate.

14. Beeswax derivatives, e.g. polyoxyethylene sorbitol beeswax. These are reaction products of beeswax with ethoxylated sorbitol of varying ethylene oxide content, forming a mixture of ether esters.

15. Vegetable waxes including carnauba and candelilla waxes.

16. Phospholipids such as lecithin and derivatives.

17. Sterols. Cholesterol, cholesterol fatty acid esters are examples thereof.

18. Amides such as fatty acid amides, ethoxylated fatty acid amides, solid fatty acid alkanolamides.

Amounts of the above listed emollients may range anywhere from about 0.5 to about 40% by weight of the total composition. Preferably the amounts of these emollients will range from about 2 to about 25%, optimally between about 5 and 15% by weight.

Humectants of the polyhydric alcohol-type may also be included in the compositions of this invention. The humectant aids in increasing the effectiveness of the emollients reduces scaling, stimulates removal of built-up scale and improves skin feel. Typical polyhydric alcohols include polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably glycerol. The amount of humectant may range anywhere from 0.5 to 20%, preferably between 1 and 15% by weight of the composition.

For improved lubricity, there may also be included one or more silicone oils or fluids which may be selected from a dimethyl polysiloxane, a methylphenyl polysiloxane and an alcohol-soluble silicone glycol copolymer. Preferred siloxanes include dimethyl polysiloxane (CTFA name: dimethicone), a polysiloxane end-blocked with trimethyl units and polydimethylcyclosiloxane, (CTFA name: cyclomethicone). The preferred siloxanes exhibit a viscosity from about 2 to 50 centistokes at 25° C. Amounts of the silicones can range up to 30% by weight of the compositions, preferably from about 1 to about 10% by weight.

Surfactants can also be included in the compositions of this invention. These may be selected from nonionic, anionic, cationic or amphoteric emulsifying agents. They may range in amount anywhere from about 0.1 to 20% by weight. A particularly preferred anionic emulsifying agent is a dimethicone copolyol phosphate available under the trademark Pecosil®. A particularly preferred nonionic emulsifying agent, especially in the formation of water-in-silicone emulsions, is cetyl dimethicone copolyol available under the trademark Abil EM-90® sold by the Goldschmidt Chemical Corporation.

The emulsions of the invention can also include thickeners/viscosifiers in amounts up to about 5% by weight of the composition. As known to those skilled in the art, the precise amount of thickeners can vary depending upon the consistency and thickness of the composition which is desired. Exemplary thickeners are xanthan gum, sodium carboxymethyl cellulose, hydroxyalkyl and alkyl celluloses, and cross-linked acrylic acid polymers such as those sold by B.F. Goodrich under the Carbopol® trademark.

Waterproofing agents may also be included in the compositions of this invention. These agents may range in amount anywhere from about 0.5 to about 10% by weight. Common waterproofing agents are polymers and copolymers based on PVP and acrylic or methacrylic esters. Specific examples are PVP/Hexadecene Copolymer (Ganex V-216®), PVP/Eicosene Copolymer (Ganex V-220®), PVP/Ethyl Methacrylate/Methacrylic Acid Copolymer, Ammonium Acrylates Copolymer, and Polyolprepolymer-2 (ex Penederm/Barnet).

Preservatives can desirably be incorporated into the cosmetic compositions of this invention to protect against the growth of potentially harmful microorganisms. While it is in the aqueous phase that microorganisms tend to grow, microorganisms can also reside in the oil phase. As such, preservatives which have solubility in both water and oil are preferably employed in the present compositions. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are methyl paraben, imidazolidinyl urea, sodium dehydroxyacetate, propyl paraben and benzyl alcohol. The preservatives should be selected having regard for the use of the composition and possible incompatibilities between the preservatives and other ingredients in the emulsion. Preservatives are preferably employed in amounts ranging from about 0.01 % to about 2% by weight of the composition.

Amounts of water in the composition may range anywhere from about 1 to about 99%, preferably from about 20 to about 90%, optimally between about 40 and 70% by weight.

Minor adjunct ingredients may also include fragrances, antifoam agents, bacteriostats, opacifiers and colorants, each in their effective amounts to accomplish their respective functions.

The following examples will more fully illustrate the embodiments of this invention. All parts, percentages and proportions referred to herein and in the appended claims are by weight unless otherwise indicated.

EXAMPLE 1

A cosmetic composition illustrative of the present invention was formulated for body use with an SPF of 21. The formulation was as follows.

| COMPONENT | WEIGHT % |
|---|---|
| Propylene Glycol Isoceteth-3 Acetate | 14.00 |
| Octyl Dodecyl neopentanoate | 14.00 |
| Titanium Dioxide | 13.00 |
| Cetyl Alcohol | 4.00 |
| Zinc Oxide | 3.00 |
| Dimethicone Copolyol Phosphate | 3.00 |
| PEG-20 Sorbitan Isostearate | 2.00 |
| Isostearic acid | 1.75 |
| Polyoxyethylene (21) Stearyl Ether | 1.50 |
| Magnesium Aluminum Silicate | 0.70 |
| Propylene Glycol | 0.50 |
| Glycerin | 0.50 |
| Iron oxides (yellow/red) at 30% in Propylene Glycol | 0.40 |
| Triethanolamine | 0.35 |
| Xanthan Gum | 0.20 |
| Polyoxyethylene (2) Stearyl Ether | 0.20 |
| Glydant Plus ® | 0.20 |
| Fragrance | 0.20 |
| Botanical Blend | 0.10 |
| Vitamin E Linoleate | 0.10 |
| Aloe Vera Gel | 0.01 |
| Green Tea | 0.01 |
| Water | qs |

The above formulation was prepared in the following manner. A reactor was charged with water and heated to 75° C. Veegum ® magnesium aluminum silicate) was dispersed in the water. After mixing for about 15 minutes, the aqueous mixture was circulated through a colloid mill at 0.010 inches. Thereafter, dimethicone copolyol phosphate, micronized zinc oxide, and glycerin/triethanolamine were sequentially added with approximately 10-15 minute mixing interval between each addition. A premix of one-half the amount of propylene glycol and xanthan gum was then added to the main batch with mixing for 20 minutes at a temperature of 75° C.

A further pair of premixes were formulated. A first of these premixes was a combination of propylene glycol isoceteth-3 acetate, octyl dodecyl neopentanoate and micronized titanium dioxide. The combination was mixed with a propeller and circulated through a colloid mill at 0.010 inches for 30 minutes. A second of the premixes was formed from cetyl alcohol, PEG-20 sorbitan isostearate, isostearic acid, polyoxyethylene (21) stearyl ether, Vitamin E Linoleate and polyoxyethylene (2) stearyl ether.

The second premix was added to the first premix and the combination heated at 75° C. for 10 minutes. This combination was then slowly added to the main batch and recirculated through a colloid mill for 15 minutes and cooled to 50° C. with the colloid mill on. The iron oxides in propylene glycol were then added. Upon cooling to 40° C., a third premix with Glydant Plus ®, the Botanical Blend, aloe vera gel and green tea were combined with half of the propylene glycol and 1% deionized water. Upon cooling to 32° C., mixing was discontinued and the mixture pumped through a 100 mesh screen.

EXAMPLE 2

A cosmetic composition according to the present invention for use on the face was formulated with an SPF of 15. The formula was as follows.

| COMPONENT | WEIGHT % |
|---|---|
| Propylene Glycol Isoceteth-3 Acetate | 13.00 |
| Titanium Dioxide | 10.00 |
| Octyl Dodecyl neopentanoate | 10.00 |
| Cetyl Alcohol | 4.00 |
| Zinc Oxide | 3.00 |
| Glycerin | 3.00 |
| Cetyl Dimethicone | 3.00 |
| Dimethicone Copolyol Phosphate | 3.00 |
| PEG-20 Sorbitan Isostearate | 2.00 |
| Polypropylene Glycol | 2.00 |
| Isostearic Acid | 1.75 |
| Polyoxyethylene (21) Stearyl Ether | 1.50 |
| Botanical Blend | 1.00 |
| Iron oxides (30% yellow/red/black) at 30% in Propylene Glycol | 0.85 |
| Magnesium Aluminum Silicate | 0.70 |
| Vitamin E Linoleate | 0.50 |
| Green Tea | 0.01 |
| Triethanolamine | 0.35 |
| Xanthan Gum | 0.20 |
| Glydant Plus | 0.20 |
| Polyoxyethylene (2) Stearyl Ether | 0.20 |
| Aloe Vera Gel | 0.01 |
| Water | qs |

Preparation of the formulation in the above Table was conducted in a manner essentially identical to that described in Example 1.

EXAMPLE 3

A series of SPF tests were conducted to evaluate the interaction of green tea with commerical sunscreens. Test product was formulated as follows:

5% Green Tea (Polyphenon 60, ex Lipton) was formulated into a gel base containing 5% oleic acid, 0.02% EDTA, 0.2% Glydant Plus ® (preservative) and Carbopol 980 ® (gellant) in a solvent system containing 1:2:1 ratio of water:ethanol:propylene glycol.

SPF TESTING IN VITRO: The above 5% Green Tea formulation was tested for in vitro SPF using a commercial instrument (Optometrics SPF 290, Optometrics Corporation, Ayre, Ma.). The instrumental SPF method has been described in a recent paper ("An Instrument for In-Vitro Determination of SPF", R. L. Sellers and F. G. Carpenter, *Cosmetics & Toiletries*, Vol. 107, October 1992, pp. 119-123), and is based on the well-known Diffey method ("A New Substrate to measure Sunscreen Protection Factors Throughout the Ultraviolet Spectrum", B. L. Diffey and J. Robson, *J. Soc. Cosm. Chem.*, 40 (3), pp. 123-133, 1989).

Using this instrument, there was obtained a very modest SPF=1.4 for the 5% Green Tea formulation. The Optometrics SPF 290 was also utilized to determine an SPF of 8 for a commercial SPF 8 sunscreen (Vaseline Intensive Care Lotion ® SPF 8) incorporating ethylhexyl p-methoxycinnamate and oxybenzone as sunscreen actives.

SPF TESTING IN VIVO: The 5% Green Tea formulation was tested for SPF on five panelists by an independent testing laboratory using standard FDA protocol. In addition to evaluating the Green Tea formulation alone, this formulation was tested in combination with the aforementioned Vaseline Intensive Care Lotion ® SPF 8 sunscreen. The procedure included applying the Green Tea formulation to a panelist's skin, allowing drying for 15 minutes and then applying the SPF 8 sunscreen. The results obtained were as follows:

| COMPOSITION | SPF |
| --- | --- |
| Green Tea Formulation | 3.0 |
| Green Tea and SPF 8 Sunscreen | 15.0 |

Based on the in vitro testing, it was expected that the Green Tea formulation would result in only very modest protection (SPF of less than 2). It was also expected that the combination with the SPF 8 sunscreen would result in little additional protection (SPF of less than 10). Instead, the obtained SPF was higher than either Green Tea or the commercial sunscreen alone, and also much greater than the expected protection from the additive combination of Green Tea with the commercial sunscreen.

EXAMPLE 4

A further sunscreen cosmetic composition according to the present invention can be prepared from the following components.

| COMPONENT | WEIGHT % |
| --- | --- |
| Ethylhexyl p-Methoxycinnamate | 7.00 |
| Glycerin | 4.00 |
| Oxybenzone | 3.00 |
| Green Tea | 3.00 |
| Alkyl Polyglycoside | 3.00 |
| Cetyl Alcohol | 2.50 |
| Glycerol Monostearate | 2.00 |
| Octyl Palmitate | 2.00 |
| Silicone Fluid | 1.50 |
| Petroleum Jelly | 1.00 |
| Methyl Paraben | 0.15 |
| Propyl Paraben | 0.10 |
| Fragrance | 0.10 |
| Antifoam | 0.01 |
| Water | qs |

EXAMPLE 5

A further sunscreen cosmetic composition according to the present invention can be prepared from the following components.

| COMPONENT | WEIGHT % |
| --- | --- |
| Hexyl Laurate | 8.00 |
| Isopropyl Myristate | 3.00 |
| Stearic Acid | 3.00 |
| Propylene Glycol | 3.00 |
| Cyclomethicone | 3.00 |
| Octyl Methoxycinnamate | 2.00 |
| Panthenol | 1.00 |
| Butyl Methoxydibenzoylmethane | 1.00 |
| Green Tea | 1.00 |
| Disodium EDTA | 0.10 |
| Fragrance | 0.10 |
| Sodium Sorbate | 0.10 |
| Water | qs |

EXAMPLE 6

A further sunscreen cosmetic composition according to the present invention can be prepared from the following components.

| COMPONENT | WEIGHT % |
| --- | --- |
| Cyclomethicone | 48.30 |
| Ethyl Alcohol | 24.10 |
| Isopropyl PPG-2 Isodeceth-7-carboxylate | 10.00 |
| Octyldimethyl PABA | 7.00 |
| Benzophenone-3 | 6.00 |
| Propylene Glycol Dicaprylate/Dicaprate | 4.00 |
| Green Tea | 0.50 |

EXAMPLE 7

A further sunscreen cosmetic composition according to the present invention can be prepared from the following components.

| COMPONENT | WEIGHT % |
| --- | --- |
| Titanium Dioxide | 15.00 |
| Zinc Oxide | 5.00 |
| PPG-3 Myristyl Ether | 5.00 |
| Methyl Glucose Sesquistearate | 5.00 |
| Mineral Oil | 5.00 |
| Hydroxylated Lanolin | 3.00 |
| Glyceryl Stearate | 3.00 |
| Green Tea | 2.00 |
| PEG-100 Stearate | 2.00 |
| Methyl Gluceth-10 | 2.00 |
| PEG-20 Methyl Glucose Sesquistearate | 0.90 |
| Phenoxyethanol | 0.50 |
| Fragrance | 0.30 |
| Water | qs |

EXAMPLE 8

A further sunscreen cosmetic composition according to the present invention can be prepared from the following components.

| COMPONENT | WEIGHT % |
| --- | --- |
| Cyclomethicone | 30.00 |
| Mineral Oil | 6.00 |
| Diisopropyl Dimerate | 5.00 |
| PEG-100 Stearate | 5.00 |
| Iron Oxide (yellow) | 1.00 |
| Iron Oxide (red) | 1.00 |
| Green Tea | 1.00 |
| PEG-3 Stearate | 0.70 |
| Zinc Oxide | 0.50 |
| Potassium Sorbate | 0.30 |
| Fragrance | 0.25 |
| Water | qs |

Although this invention has been described with reference to specific examples, it will be apparent to one skilled in the art that various modifications may be made thereto which fall within the scope and purview of the invention.

What is claimed is:

1. A sunscreen cosmetic having a sunscreen system comprising:
   (i) from about 0.001 to about 20% by weight of green tea;
   (ii) from about 0.001 to about 25% by weight of a sunscreen compound which is effective to at least partially block ultraviolet radiation from harming human skin; and
   (iii) from about 30 to 99.9% by weight of a pharmaceutically acceptable carrier.

2. The sunscreening cosmetic composition according to claim 1, wherein the sunscreen compound is an organic material selected from the group consisting of para-amino benzoates; salicylates; cinnamates; benzophenones; coumarins; azoles; menthyl anthralinates; polyethylene; polyamides and mixtures thereof.

3. The sunscreening cosmetic composition according to claim 1, wherein the sunscreen compound is inorganic and selected from the group consisting of titanium dioxide, zinc oxide, iron oxide and combinations thereof.

4. A sunscreen cosmetic composition having a sunscreen system comprising:

(i) from about 0.001 to 5% by weight of green tea; and (ii) from about 0.001 to about 25% by weight of titanium dioxide having a particle size no higher than 200 nm which is an ultraviolet ray-blocking material inhibiting absorption within the wavelength region between 290 and 420 nm; and (iii) from about 30 to 99.9% by weight of a pharmaceutically acceptable carrier.

5. The sunscreen cosmetic composition according to claim 4, wherein the titanium dioxide is present in an amount from about 10 to about 50% by weight and has an average particle size less than 35 nm.

* * * * *